(12) United States Patent
Nakasaki

(10) Patent No.: US 8,703,423 B2
(45) Date of Patent: Apr. 22, 2014

(54) METHOD OF DETECTING A FUNCTIONAL FILAMENTOUS FUNGUS, METHOD OF EVALUATING A PRODUCT CONTAINING A FUNCTIONAL FILAMENTOUS FUNGUS, AND PRIMER PAIR

(75) Inventor: Kiyohiko Nakasaki, Yokohoma (JP)

(73) Assignee: National University Corporation Shizuoka University, Shizuoka-shi (JP)

( * ) Notice: Subject to any disclaimer, the term of this patent is extended or adjusted under 35 U.S.C. 154(b) by 274 days.

(21) Appl. No.: 13/060,000

(22) PCT Filed: Aug. 20, 2009

(86) PCT No.: PCT/JP2009/064598
§ 371 (c)(1),
(2), (4) Date: Apr. 6, 2011

(87) PCT Pub. No.: WO2010/021369
PCT Pub. Date: Feb. 25, 2010

(65) Prior Publication Data
US 2011/0177519 A1 Jul. 21, 2011

(30) Foreign Application Priority Data

Aug. 22, 2008 (JP) ................................. 2008-214394

(51) Int. Cl.
*C12Q 1/68* (2006.01)
*C12P 19/34* (2006.01)
*C07H 21/04* (2006.01)

(52) U.S. Cl.
USPC ........ 435/6.12; 435/6.1; 435/6.11; 536/24.33

(58) Field of Classification Search
None
See application file for complete search history.

(56) References Cited

U.S. PATENT DOCUMENTS

2008/0248058 A1 10/2008 Nakasaki et al.

FOREIGN PATENT DOCUMENTS

| EP | 0 823 202 A1 | 2/1998 |
| JP | 2007-174973 A | 7/2007 |
| JP | 2007-268471 A | 10/2007 |
| JP | 2008-214394 A | 9/2008 |
| WO | WO-97/31521 A1 | 9/1997 |
| WO | WO-2006/085567 A1 | 8/2006 |

OTHER PUBLICATIONS

Nakasaki et al., "*Coprinellus curtus* (Hitoyo-take) Prevents Diseases of Vegetables Caused by Pathogenic Fungi," *FEMS Microbiol Lett.*, 275:286-291 (2007).
Nakasaki, "Organic Manure Which Enables Prevention of Plant Diseases and Rapid Plant Growth without Argicultural Chemicals," *New Food Industry*, 49(11):21-27 (2007).
Nakasaki, "Rapid and Simple Method for Evaluation of Compost Maturity by Analyzing Microbial Community," *Journal of Resources and Environment*, 42(13):95-99 (2006).
International Preliminary Report on Patentability for Application No. PCT/JP2009/064598, dated Aug. 13, 2010.
International Search Report for Application No. PCT/JP2009/064598, dated Sep. 29, 2009.

*Primary Examiner* — Young J Kim
(74) *Attorney, Agent, or Firm* — Marshall, Gerstein & Borun LLP

(57) ABSTRACT

The present invention provides a method of detecting a functional filamentous fungus, wherein the functional filamentous fungus, *Coprinellus curtus*, in a sample is detected using at least one polynucleotide selected from the group consisting of polynucleotides having a nucleotide sequence shown in SEQ ID NO: 1, SEQ ID NO: 2, SEQ ID NO: 3 or SEQ ID NO: 4 and polynucleotides having a nucleotide sequence complementary thereto, and polynucleotides having a nucleotide sequence substantially homologous to these sequences; and a method of evaluating a product containing a functional filamentous fungus wherein the existence or concentration of the functional filamentous fungus, *Coprinellus curtus*, in a product containing a functional filamentous fungus is evaluated.

14 Claims, 8 Drawing Sheets

FIG.1

```
  1 tttccgtagg tgaacctgcg gaaggatcat taacgaataa ctatggtgtt ggttgtagct
 61 gcctcctcgg aggaatgtgc acgcccgcca tttttatctt tccacctgtg caccgactgt
121 aggtctggat aactctcgcc tcacggcaga tgcgaggatt ggcctctgtg cctctcctcg
181 aatttccagg ctctacgtct tttacacacc ccaatagtat gatatagaat gtagtcaatg
241 ggcttcttag cctataaaac actatacaac tttcagcaac ggatctcttg gctctcgcat
301 cgatgaagaa cgcagcgaaa tgcgataagt aatgtgaatt gcagaattca gtgaatcatc
361 gaatctttga acgcaccttg cgctccttgg tattccgagg agcatgcctg tttgagtgtc
421 attaaattct caacctcgcc agttttctga actgcgtcga ggcttggatt gtggggtttt
481 gtgcaggctg cctcagcgtg gtctgctccc ctgaaatgca ttagcgagtt catactgagc
541 tccgtctatc ggtgtgataa ttatctacgc cgttagtcga gttcagactt gcttctaacc
601 gtccgcaagg acaactcttg acaatttgac ctcaaatcag gtaggactac ccgctgaact
661 taa
```

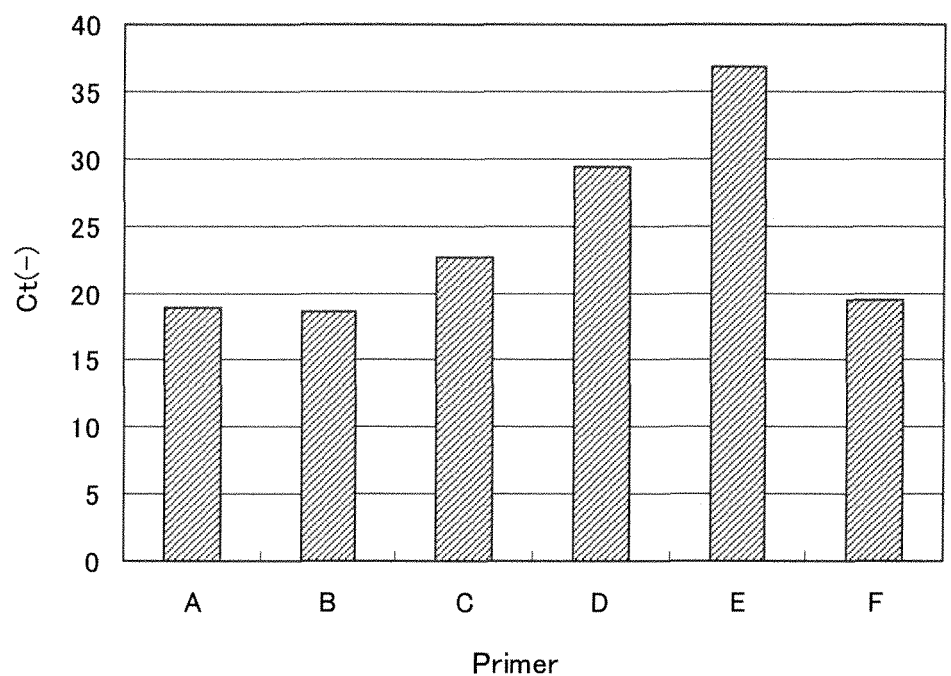

SEQUENCE LISTING

<160> NUMBER OF SEQ ID NOS: 12

<210> SEQ ID NO 1
<211> LENGTH: 23
<212> TYPE: DNA
<213> ORGANISM: Artificial
<220> FEATURE:
<223> OTHER INFORMATION: primer_GM2125F

```
<400> SEQUENCE: 1
gtgttgcatg tagctgcctc ctc                                          23

<210> SEQ ID NO 2
<211> LENGTH: 25
<212> TYPE: DNA
<213> ORGANISM: Artificial
<220> FEATURE:
<223> OTHER INFORMATION: primer_GM2152R

<400> SEQUENCE: 2
tgacgcgaga gttatccaga cctac                                        25

<210> SEQ ID NO 3
<211> LENGTH: 23
<212> TYPE: DNA
<213> ORGANISM: Artificial
<220> FEATURE:
<223> OTHER INFORMATION: primer_GM2127F

<400> SEQUENCE: 3
gtgttggttg tagctgcctc ctc                                          23

<210> SEQ ID NO 4
<211> LENGTH: 21
<212> TYPE: DNA
<213> ORGANISM: Artificial
<220> FEATURE:
<223> OTHER INFORMATION: primer_GM2172R

<400> SEQUENCE: 4
tggtaattcg aggagaggca c                                            21

<210> SEQ ID NO 5
<211> LENGTH: 17
<212> TYPE: DNA
<213> ORGANISM: Artificial
<220> FEATURE:
<223> OTHER INFORMATION: primer_GM2182R

<400> SEQUENCE: 5
acaggtgcca atcctcg                                                 17

<210> SEQ ID NO 6
<211> LENGTH: 22
<212> TYPE: DNA
<213> ORGANISM: Artificial
<220> FEATURE:
<223> OTHER INFORMATION: primer_GM21715F

<400> SEQUENCE: 6
gtgcctctcc tcgaatttcc ag                                           22

<210> SEQ ID NO 7
<211> LENGTH: 15
<212> TYPE: DNA
<213> ORGANISM: Artificial
<220> FEATURE:
<223> OTHER INFORMATION: primer_GM21157R

<400> SEQUENCE: 7
acgacgccca ttgac                                                   15

<210> SEQ ID NO 8
<211> LENGTH: 16
<212> TYPE: DNA
```

```
<213> ORGANISM: Artificial
<220> FEATURE:
<223> OTHER INFORMATION: primer_GM21815F

<400> SEQUENCE: 8
gattgtccac tgtgcc                                                      16

<210> SEQ ID NO 9
<211> LENGTH: 15
<212> TYPE: DNA
<213> ORGANISM: Artificial
<220> FEATURE:
<223> OTHER INFORMATION: primer_GM21158R

<400> SEQUENCE: 9
acgaagccca ttgac                                                       15

<210> SEQ ID NO 10
<211> LENGTH: 15
<212> TYPE: DNA
<213> ORGANISM: Artificial
<220> FEATURE:
<223> OTHER INFORMATION: primer_GM2110F

<400> SEQUENCE: 10
ctgaactgcg tcgag                                                       15

<210> SEQ ID NO 11
<211> LENGTH: 17
<212> TYPE: DNA
<213> ORGANISM: Artificial
<220> FEATURE:
<223> OTHER INFORMATION: primer_GM2111R

<400> SEQUENCE: 11
gcaagactga actcgac                                                     17

<210> SEQ ID NO 12
<211> LENGTH: 663
<212> TYPE: DNA
<213> ORGANISM: Coprinellus curtus GM-21

<400> SEQUENCE: 12
tttccgtagg tgaacctgcg gaaggatcat taacgaataa ctatggtgtt ggttgtagct       60
gcctcctcgg aggaatgtgc acgcccgcca tttttatctt tccacctgtg caccgactgt      120
aggtctggat aactctcgcc tcacggcaga tgcgaggatt ggcctctgtg cctctcctcg      180
aatttccagg ctctacgtct tttacacacc ccaatagtat gatatagaat gtagtcaatg      240
ggcttcttag cctataaaac actatacaac tttcagcaac ggatctcttg gctctcgcat      300
cgatgaagaa cgcagcgaaa tgcgataagt aatgtgaatt gcagaattca gtgaatcatc      360
gaatctttga acgcaccttg cgctccttgg tattccgagg agcatgcctg tttgagtgtc      420
attaaattct caacctcgcc agttttctga actgcgtcga ggcttggatt gtggggggttt     480 gtgcaggctg cctcagcgtg gtctgctccc ctgaaatgca ttagcgagtt catactgagc      540
tccgtctatc ggtgtgataa ttatctacgc cgttagtcga gttcagactt gcttctaacc      600
gtccgcaagg acaactcttg acaatttgac ctcaaatcag gtaggactac ccgctgaact      660
taa                                                                   663
```

METHOD OF DETECTING A FUNCTIONAL FILAMENTOUS FUNGUS, METHOD OF EVALUATING A PRODUCT CONTAINING A FUNCTIONAL FILAMENTOUS FUNGUS, AND PRIMER PAIR

TECHNICAL FIELD

The present invention relates to a method of detecting a functional filamentous fungus; a method of evaluating a product containing a functional filamentous fungus; and a primer pair.

BACKGROUND ART

Filamentous fungi, namely molds, are known to have various functions, and for example, plant diseases are known to be caused by pathogenic filamentous fungi. Pathogenic filamentous fungi are the cause of diseases such as damping-off, root rot, leaf rot and wilt in agricultural products including many vegetables such as cabbage, cucumber, tomato, eggplant and rape leaf and rice plants, as well as in flowers, trees, turf and others. As such pathogenic filamentous fungi, those belonging to the genus *Rhizoctonia*, the genus *Fusarium*, the genus *Pythium*, the genus *Trichoderma* and the genus *Sclerotium* are well known.

Examples of a method of controlling plant disease which is effective against such pathogenic filamentous fungi include those plant disease control agents using a microorganism, specifically a filamentous fungus (for example, WO 97/31521 and WO 2006/085567). It is generally known that the suitable growth conditions are different between bacteria and filamentous fungi. Therefore, plant disease control agents utilizing, instead of a bacterium, a functional filamentous fungus capable of demonstrating plant disease-controlling function under the suitable growth condition for a pathogenic filamentous fungus are expected to have a more superior effect compared to those plant disease control agents utilizing bacteria. Among such plant disease control agents, one which utilizes a filamentous fungus belonging to the family Coprinaceae has a superior function (see WO 2006/085567).

By the way, in order to utilize such a functional filamentous fungus as a plant disease control agent, it is necessary that the functional filamentous fungus be made to exist in a soil or compost at an appropriate density so as to demonstrate an appropriate plant disease-controlling function, and that the functional filamentous fungus maintains this function.

In order to conveniently utilize a prescribed function of a functional filamentous fungus, a product containing the functional filamentous fungus is produced in some cases by inoculating the functional filamentous fungus to a soil, compost, solid medium or immobilization carrier. When such a functional filamentous fungus-containing product is prepared, it is indispensable to appropriately monitor the concentration of the functional filamentous fungus during the process of production, storage, transport or the like.

In recent years, techniques which detect and identify bacteria using a molecular biological means have been developed.

For example, Japanese Patent Application Laid-Open (JP-A) No. 2007-268471 provides a method for detecting methane-producing bacteria and acid-producing bacteria relating to methanogenesis in sludge for methane fermentation treatment, such as organic waste and waste water and evaluating the activity of the bacteria, thereby disclosing a suitable operation management index of a methane fermentation apparatus and a process control method. This method utilizes a method of exhaustively and quantitatively detecting Eubacteria group to which acid-producing bacteria belong or methanogen group having methane-producing ability, and includes quantitatively detecting and monitoring over time the DNA and RNA concentrations using a PCR method.

Further, JP-A No. 2007-174973 discloses a technique whereby DNA contained in a sample of, for example, agricultural product (crops and vegetables), livestock product (meat), fishery product (fish and shellfish), hair, body fluid or microorganism can be amplified and analyzed highly accurately, promptly and simply, as well as at a low cost. This method includes the step of amplifying the DNA in a sample by PCR, which step is conducted by multiplexing using SSR primer pair.

However, in addition to a desired functional filamentous fungus, a variety of filamentous fungi and bacteria are present in a soil and compost. Monitoring of only a specific functional filamentous fungus in such a soil or compost requires a detection method which shows very high specificity. Also required is an evaluation method which appropriately evaluates a product containing the functional filamentous fungus obtained by inoculation of the functional filamentous fungus.

DISCLOSURE OF THE INVENTION

Means for Solving the Problems

An object of the present invention is to provide a method of detecting a functional filamentous fungus whereby the functional filamentous fungus, *Coprinellus curtus*, can be detected at high accuracy; and a method of evaluating a product containing a functional filamentous fungus.

The first aspect of the present invention provides a method of detecting a functional filamentous fungus in which a functional filamentous fungus, *Coprinellus curtus*, in a sample is detected by using at least one polynucleotide selected from the group consisting of: (1) a polynucleotide having the nucleotide sequence shown in SEQ ID NO: 1, polynucleotides having a nucleotide sequence complementary thereto, and polynucleotides having a nucleotide sequence substantially homologous to these sequences; (2) a polynucleotide having the nucleotide sequence shown in SEQ ID NO: 2, polynucleotides having a nucleotide sequence complementary thereto, and polynucleotides having a nucleotide sequence substantially homologous to these sequences; (3) a polynucleotide having the nucleotide sequence shown in SEQ ID NO: 3, polynucleotides having a nucleotide sequence complementary thereto, and polynucleotides having a nucleotide sequence substantially homologous to these sequences; and (4) a polynucleotide having the nucleotide sequence shown in SEQ ID NO: 4, polynucleotides having a nucleotide sequence complementary thereto, and polynucleotides having a nucleotide sequence substantially homologous to these sequences.

The second aspect of the present invention provides a method of evaluating a product containing the functional filamentous fungus, *Coprinellus curtus*, which method includes carrying out quantitative PCR on a sample from the functional filamentous fungus-containing product using a primer pair including a polynucleotide having the nucleotide sequence shown in SEQ ID NO: 1 or SEQ ID NO: 3 or a nucleotide sequence substantially homologous thereto and a polynucleotide having the nucleotide sequence shown in SEQ ID NO: 2 or SEQ ID NO: 4 or a nucleotide sequence substantially homologous thereto; and evaluating, based on the results of the quantitative PCR, the presence or the concentration of the functional filamentous fungus, *Coprinellus curtus*, in the functional filamentous fungus-containing product.

The third aspect of the present invention provides a primer pair comprising the following polynucleotides: (1) a polynucleotide having a nucleotide sequence shown in SEQ ID NO: 1 or SEQ ID NO: 3 or one substantially homologous thereto and capable of recognizing the functional filamentous fungus, *Coprinellus curtus*; and (2) a polynucleotide having a nucleotide sequence shown in SEQ ID NO: 2 or SEQ ID NO: 4 or one substantially homologous thereto and capable of recognizing the functional filamentous fungus, *Coprinellus curtus*.

The fourth aspect of the present invention provides one of the following polynucleotides or a polynucleotide set comprising at least two selected from the group consisting of the following polynucleotides: (1) a polynucleotide having the nucleotide sequence shown in SEQ ID NO: 1 or a nucleotide sequence complementary thereto, or a polynucleotide having a nucleotide sequence which is substantially homologous to these sequences and is capable of recognizing the functional filamentous fungus, *Coprinellus curtus*; (2) a polynucleotide having the nucleotide sequence shown in SEQ ID NO: 2 or a nucleotide sequence complementary thereto, or a polynucleotide having a nucleotide sequence which is substantially homologous to these sequences and is capable of recognizing the functional filamentous fungus, *Coprinellus curtus*; (3) a polynucleotide having the nucleotide sequence shown in SEQ ID NO: 3 or a nucleotide sequence complementary thereto, or a polynucleotide having a nucleotide sequence which is substantially homologous to these sequences and is capable of recognizing the functional filamentous fungus, *Coprinellus curtus*; and (4) a polynucleotide having the nucleotide sequence shown in SEQ ID NO: 4 or a nucleotide sequence complementary thereto, or a polynucleotide having a nucleotide sequence which is substantially homologous to these sequences and is capable of recognizing the functional filamentous fungus, *Coprinellus curtus*.

BRIEF DESCRIPTION OF THE DRAWINGS

FIG. 1 is the sequence of the GM-21 strain used to obtain the primer set according to the present invention.

FIG. 2 is a graph showing the Ct values of the real-time PCR using the GM-21 strain according to Example 1.

BEST MODE FOR CARRYING OUT THE INVENTION

Figure 3:
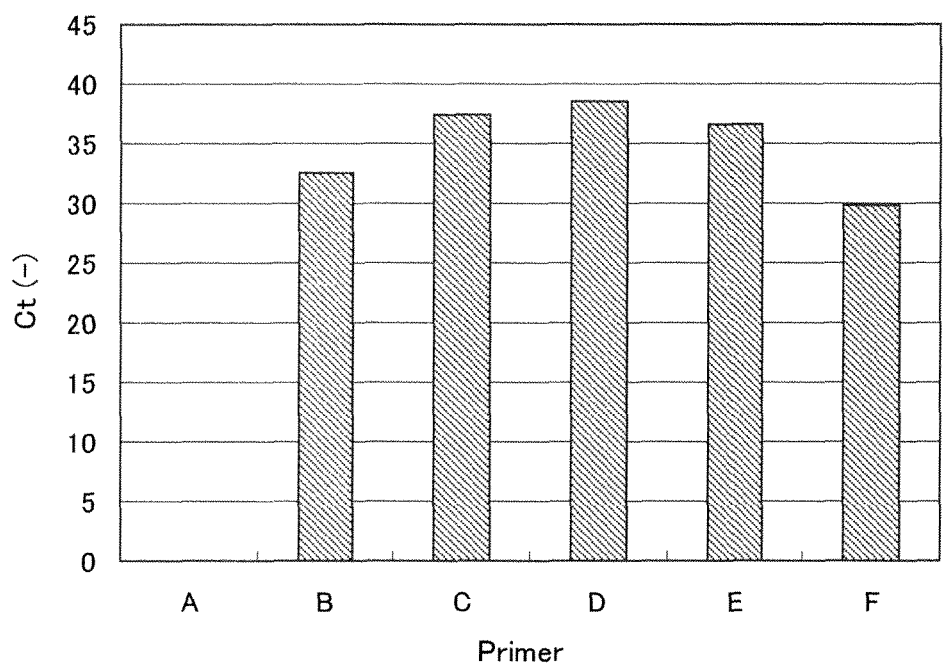
FIG. 3 is a graph showing the Ct values of the real-time PCR using the ultrapure water sample according to Example 1.

The method of detecting the functional filamentous fungus, *Coprinellus curtus*, according to the present invention is a method according to which the functional filamentous fungus, *Coprinellus curtus*, in a sample is detected by using at least one polynucleotide selected from the group consisting of: (1) a polynucleotide having the nucleotide sequence GTGTTGCATGTAGCTGCCTCCTC (GM2125F: SEQ ID NO: 1), polynucleotides having a nucleotide sequence complementary thereto, and polynucleotides having a nucleotide sequence substantially homologous to these sequences; (2) a polynucleotide having the nucleotide sequence TGACGCGAGAGTTATCCAGACCTAC (GM2152R: SEQ ID NO: 2), polynucleotides having a nucleotide sequence complementary thereto, and polynucleotides having a nucleotide sequence substantially homologous to these sequences; (3) a polynucleotide having the nucleotide sequence GTGTTGGTTGTAGCTGCCTCCTC (GM2127F: SEQ ID NO: 3), polynucleotides having a nucleotide sequence complementary thereto, and polynucleotides having a nucleotide sequence substantially homologous to these sequences; and (4) a polynucleotide having the nucleotide sequence TGGTAATTCGAGGAGAGGCAC (GM2172R: SEQ ID NO: 4), polynucleotides having a nucleotide sequence complementary thereto, and polynucleotides having a nucleotide sequence substantially homologous to these sequences.

Since these polynucleotides exhibit high specificity to the functional filamentous fungus, *Coprinellus curtus*, the functional filamentous fungus, *Coprinellus curtus*, in a sample is accurately detected by using these polynucleotides.

Further, the term "step" used herein includes not only a discrete step, but also steps which cannot be clearly distinguished from another step, as long as the expected effect of the pertinent step can be achieved.

In addition, ranges indicated herein with "to" include the numerical values before and after "to".

Since the above-described GM2125F, GM2127F, GM2152R, GM2172R or a combination thereof are distinctively detected also from their closely-related species, they are extremely suitable for highly accurately and specifically detecting the functional filamentous fungus of interest, *Coprinellus curtus*.

In the region of the 663 bases region including the sequence 18S (partial), ITS1, 5.8S, ITS2, and 26S (partial) of the GM-21 strain (SEQ ID NO: 12) shown in FIG. 1, the GM2125F, GM2127F, GM2152R and GM2172R correspond to the 46th to 68th bases (SEQ ID NO: 1 and SEQ ID NO: 3), 119th to 143rd bases (SEQ ID NO: 2), and 168th to 188th bases (SEQ ID NO: 4). The conservation of these regions is relatively low and these regions have particularly high specificity to *Coprinellus curtus*. Therefore, by using GM2125F, GM2127F, GM2152R or GM2172R corresponding to these regions or a combination of these sequences, *Coprinellus curtus* may be accurately detected.

In addition, the respective sequences which are complementary to the above-described sequences and the respective sequences which are substantially homologous to these complementary sequences may also be used for accurately detecting the functional filamentous fungus, *Coprinellus curtus*, and such sequences may be employed in the detection method according to the present invention in the same manner as GM2125F, GM2127F, GM2152R and GM2172R.

Here, a substantially homologous sequence means a sequence having a homology by which the functional filamentous fungus, *Coprinellus curtus*, can be recognized to the same extent as in the case of respective sequences of GM2125F, GM2127F, GM2152R and GM2172R or sequences respectively complementary thereto. Examples of such sequences include sequences including a substitution, deletion or addition of several bases in an amount of from approximately 1 to 5 bases. Examples of such nucleotide sequences which are substantially homologous having only a few different bases and can recognize the functional filamentous fungus, *Coprinellus curtus*, include polynucleotides having a nucleotide sequence which hybridizes with the GM2125F, GM2127F, GM2152R, GM2172R or a sequence complementary thereto under ordinary hybridization conditions; for example, in which hybridization is performed using 4×SSC at 65° C., followed by washing with 0.1×SSC at 65° C. for 1 hour.

Among the sequences substantially homologous to the respective sequences of GM2125F, GM2127F, GM2152R and GM2172R or the respective sequences complementary to each of those sequences, examples of the preferred sequence include sequences which can be amplified under the PCR conditions indicated in Table 1 below, which sequences have the same sequence as the above-described respective sequences of GM2125F, GM2127F, GM2152R and GM2172R or sequences that are respectively complementary thereto, except that from 1 to 3 bases at the 3'-end are substituted or added, or from 1 to 5 bases at the 5'-end are substituted or added, or from 1 to 5 consecutive bases are deleted from each end. Any of such substantially homologous sequences may be used in a variety of detection methods including the PCR technique in the same manner as the above-described sequences of GM2125F, GM2127F, GM2152R and GM2172R.

TABLE 1

| | Number of Cycles | Temperature (° C.) | Time (s) |
|---|---|---|---|
| Initial Denaturation | — | 90-98 | 10 |
| Denaturation | 40 | 80-98 | 5 |
| Annealing and Elongation | | 50-70 | 20 |

Therefore, one of the following polynucleotides or a combination of two or more of these (polynucleotide set) is used in the detection method according to the present invention to accurately detect the functional filamentous fungus, *Coprinellus curtus*:

(1) a polynucleotide having the nucleotide sequence shown in SEQ ID NO: 1 or a nucleotide sequence complementary thereto, or a polynucleotide having a nucleotide sequence which is substantially homologous to these sequences and capable of recognizing the functional filamentous fungus, *Coprinellus curtus*;

(2) a polynucleotide having the nucleotide sequence shown in SEQ ID NO: 2 or a nucleotide sequence complementary thereto, or a polynucleotide having a nucleotide sequence which is substantially homologous to these sequences and capable of recognizing the functional filamentous fungus, *Coprinellus curtus*;

(3) a polynucleotide having the nucleotide sequence shown in SEQ ID NO: 3 or a nucleotide sequence complementary thereto, or a polynucleotide having a nucleotide sequence which is substantially homologous to these sequences and capable of recognizing the functional filamentous fungus, *Coprinellus curtus*;

(4) a polynucleotide having the nucleotide sequence shown in SEQ ID NO: 4 or a nucleotide sequence complementary thereto, or a polynucleotide having a nucleotide sequence which is substantially homologous to these sequences and capable of recognizing the functional filamentous fungus, *Coprinellus curtus*.

The polynucleotide set contains two or more of the polynucleotides selected from the above (1) to (4) and includes a combination appropriately selected in accordance with an object which is not restricted to the detection method of the present invention.

Further, used in the detection method according to the present invention in which PCR method is employed to particularly accurately detect the functional filamentous fungus, *Coprinellus curtus*, is a primer pair including the following polynucleotides:

(a) a polynucleotide having a nucleotide sequence shown in SEQ ID NO: 1 or SEQ ID NO: 3 or one substantially homologous thereto and capable of recognizing the functional filamentous fungus, *Coprinellus curtus*; and (b) a polynucleotide having a nucleotide sequence shown in SEQ ID NO: 2 or SEQ ID NO: 4 or one substantially homologous thereto and capable of recognizing the functional filamentous fungus, *Coprinellus curtus*.

The functional filamentous fungus, *Coprinellus curtus*, to be detected in the method of detecting a functional filamentous fungus according to the present invention is preferably *Coprinellus curtus* having a plant disease-controlling effect, and from the standpoints of the stability in the plant disease control and the detection accuracy, it is preferably GM-21 (NITE BP-37). Since this particularly preferred *Coprinellus curtus* has superior plant disease-controlling function, it is particularly preferably used as a plant disease control agent.

In order to demonstrate superior plant disease-controlling function, it is required that this preferred *Coprinellus curtus* exist at an appropriate amount. By applying the present invention, whether or not the expected plant disease-controlling function may be obtained can be simply evaluated, for example, by accurately detecting this *Coprinellus curtus* using the later-described quantitative PCR. By inoculating this filamentous fungus to a soil, compost, solid culture or the like and allowing it to proliferate in advance, the filamentous fungus can be included a soil, compost, solid culture or the like which has a plant disease-controlling effect.

Samples in the present invention are not particularly restricted, and examples thereof include those in the form of a solid phase, aqueous phase, colloid, powder, dry matter or the like where the functional filamentous fungus to be detected can exist. For example, the sample may also be at least one selected from the group consisting of a soil, compost sample, cultured sample and immobilized sample, in which a functional filamentous fungus can exist.

The term "compost" in the present invention is manure obtained by allowing an organic waste to decompose and mature. The term "composting" means a step in which organic matters in an organic waste are subjected to a degradation treatment by the actions of microorganisms so as to be converted into a state suitable for application to agricultural land. A "composting treatment" generally means to retain organic matters under appropriate aeration and stirring conditions for a prescribed time period, thereby allowing fermentation of the organic matters by microorganisms. The term "compost" used herein encompasses not only those composts in a fully-matured state in which the organic matters are completely degraded with the progress of decomposition and maturation, but also for those in an immature state.

Examples of organic waste used in the composting include kitchen garbage, sewage sludge and livestock excrements, and fish meal, poultry manure, cow manure, oil cake, sawdust, wood chips, vegetable debris, fallen leaves, sludge or a combination of two or more thereof is commonly used.

Further, as the seed microorganisms used in the composting, a formulation or a compost product itself which contains miscellaneous microorganisms such as bacteria and actinomycetes is used. As such seed microorganisms used in the composting, commercially-available ones may be used as they are.

The cultured sample is a culture obtained by culturing microorganisms using organic matters as their source of nutrition and refers to a sample obtained by allowing microorganisms to ferment by adjusting the water content of a solid substrate, such as rice bran, wheat bran or bean-surd less, and also, as appropriate, adjusting the nutritional content. Further, the immobilized sample refers to a sample constituted by microorganisms and a carrier to which the microorganisms may be immobilized. Examples of the carrier include a porous matter such as pearlite, vermiculite, zeolite, diatomaceous earth, Kanumatsuchi or a combination thereof; mineral powder such as talc, clay, calcium carbonate or a combination thereof; macromolecular compound such as polyvinyl alcohol; and naturally-occurring macromolecular compound such as xanthan gum, alginic acid or a combination thereof, and these may be employed individually or in combination of two or more thereof.

These samples may be prepared as appropriate in accordance with the form thereof. For example, in cases where the sample is in the form of an aqueous phase, it may also be diluted to an appropriate concentration. In cases where the sample is in the form of a solid phase, powder or dry matter, it may also be suspended or swollen in an appropriate aqueous medium.

Further, the later-described functional compost may also be used as the sample. The functional compost will be described later.

It is preferred that the detection method according to the present invention include a step of preparing a nucleic acid sample capable of hybridizing to the above-described polynucleotide from these samples. As the method of preparing such a nucleic acid sample, for example, a sample suspension may be prepared using a reagent having an appropriate salt concentration, followed by DNA extraction. For the DNA extraction from these samples, a known method is used in accordance with the form of the samples. Further, for extracting DNA directly from a solid sample such as a soil or compost, a commercially available kit may also be used, and examples of such kit include ISOIL for Beads Beating kit (Nippon Gene Co.), which is readily available for those skilled in the art.

The method of detecting a functional filamentous fungus according to the present invention uses at least one of the above-described polynucleotides in order to detect the functional filamentous fungus, *Coprinellus curtus*, in these samples, and the polynucleotide(s) may be appropriately selected in accordance with the mode of the molecular biological means employed in the detection.

Examples of the molecular biological means which may be applied in the method of detecting a functional filamentous fungus according to the present invention include a variety of means well-known in the art using, for example, Southern blot, Northern blot, dot blot, in situ hybridization, and/or the PCR method, and the molecular biological means is not particularly restricted.

From the standpoints of detection accuracy and manageability, among detection methods using such means, it is preferred that the detection method according to the present invention include performing PCR using a primary pair including a polynucleotide having GM2125F (SEQ ID NO: 1) or a nucleotide sequence substantially homologous thereto and a polynucleotide having GM2152R (SEQ ID NO: 2) or a nucleotide sequence substantially homologous thereto. It is most preferred that the detection method according to the present invention include performing PCR using a primary pair including GM2125F and GM2152R.

Examples of the PCR method used include a quantitative PCR method. In an ordinary PCR method, a nucleic acid test sample prepared from a sample is brought into contact with a pair of primers and intermittent amplification reactions are repeated under a set of polymerase chain reaction conditions. In this case, the amplification reaction conditions may be set as appropriate in accordance with the common technical knowledge and empirical rules in the art. A nucleic acid region having a specific fragment length which corresponds to the length between the used primer pair (between the 3'-end primer and the 5'-end primer) is specifically amplified.

Whether or not the amplified nucleic acid is the desired nucleic acid sequence can be confirmed by, for example, verifying the fragment length using a method well-known in the art. Examples of such confirmation method include electrophoresis, as well as hybridization method in which a probe or the like specific to the fragment is used.

Since the amount of amplified nucleic acid is closely correlated with the amount of microorganisms (filamentous fungi in the present invention) in the sample, the amount may be determined based on the quantitative value of the amplified nucleic acid. According to quantitative PCR method, the amount of the desired nucleic acid can be verified using as an index the amplification degree of nucleic acid having a known amount.

Examples of other method include FISH method. In FISH method, a probe is labeled to prepare a labeled FISH probe which is then mixed with a test sample, and the thus obtained mixture is subjected to hybridization under a condition in which binding between a target nucleic acid in the cell and the FISH probe takes place. The amount of bacteria is measured by identifying the detected subject based on whether or not a fluorescence signal can be obtained from the hybridized probes observing under a fluorescence microscope. Examples of the label include fluorescent dyes, radioactive isotopes and chemiluminescents such as digoxigenin (DIG).

The detection method according to the present invention includes, after the PCR step, determining the amount of the filamentous fungus of interest from the amount of the amplified nucleic acid based on a calibration curve. By this, the presence or absence of the functional filamentous fungus of interest, *Coprinellus curtus*, in the sample and the amount thereof can be accurately determined.

In this manner, the method of detecting a functional filamentous fungus according to the present invention can accurately detect the functional filamentous fungus of interest, *Coprinellus curtus*. At the same time, this detection method can also be employed as an evaluation method of a product containing a functional filamentous fungus (functional filamentous fungus-containing product). Particularly in cases where quantitative PCR is used, the detection method according to the present invention may be preferably employed in evaluating a functional filamentous fungus-containing product produced by inoculation of the functional filamentous fungus, *Coprinellus curtus*, in advance.

The method of evaluating a functional filamentous fungus-containing product according to the present invention includes carrying out quantitative PCR on a sample from the functional filamentous fungus-containing product using a primer pair including a polynucleotide having GM2125F or GM2127F, or a nucleotide sequence substantially homologous thereto, and a polynucleotide having GM2152R or GM2172R, or a nucleotide sequence substantially homologous thereto; and evaluating, based on the results of the quantitative PCR, the presence or the concentration of the functional filamentous fungus, *Coprinellus curtus*, in the functional filamentous fungus-containing product.

By using the primer pair described above, the functional filamentous fungus, *Coprinellus curtus*, can be accurately detected; therefore, in a functional filamentous fungus-containing product, evaluation of whether or not the inoculated functional filamentous fungus is maintained and of how the concentration thereof changes can be performed accurately and simply. Consequently, it becomes easy to produce a functional filamentous fungus-containing product having a superior function under appropriate control and to store and maintain the produced functional filamentous fungus-containing product.

The polynucleotide to be used may be any of the above-described polynucleotides in the same manner as in the above-described detection method, and it is preferred that the polynucleotide be a primer pair including GM2125F and GM2152R since a functional filamentous fungus-containing product can be accurately evaluated.

The above-described evaluation may be any evaluation by which the presence or the concentration of the functional filamentous fungus. *Coprinellus curtus*, in a functional filamentous fungus-containing product is evaluated, and may also be one by which not only the presence or the concentration of the filamentous fungus at a certain point of time, but also a change over time in the number of the fungus or the concentration thereof, are evaluated.

The functional filamentous fungus-containing product in the present evaluation method means a product in which the above-described functional filamentous fungus may exist, and the "samples" explained in the above-described detection method are the functional filamentous fungus-containing products as they are. In addition, from the standpoints of the proliferation rate of the filamentous fungus and the effect as a plant disease control agent, it is preferred that the functional filamentous fungus-containing product be a functional compost.

With regard to the method of producing the functional filamentous fungus-containing product, the product may be easily produced, for example, by inoculating a prescribed amount of functional filamentous fungus to a prescribed amount of a soil. Particularly, in the case of functional compost, from the standpoint of the production efficiency, a functional compost obtained in accordance with the production method described below is preferred.

Examples of preferred method of producing a functional compost include one which includes inoculating a compost with a filamentous fungus having a function and culturing it to allow the filamentous fungus selectively to proliferate. According to this method, because of the difference between a filamentous fungus and bacteria in their active environments, a filamentous fungus may be more selectively and efficiently proliferated in compost than bacteria. Consequently, the grown filamentous fungus may be stably established in the compost, so that a functional compost can be efficiently produced.

Further, another preferred method of producing a functional compost may be a method which includes inoculating a filamentous fungus having a function into a compost containing bacteria that are able to grow in coexistence with the filamentous fungus, which bacteria can be active in the growth conditions of the filamentous fungus, with the activities of bacteria other than the aforementioned bacteria able to grow in coexistence with the filamentous fungus being restricted in the compost; and culturing the filamentous fungus in the compost to selectively proliferate the filamentous fungus together with the aforementioned bacteria able to grow in coexistence therewith.

According to this method, not only are the activities of bacteria other than the bacteria able to grow in coexistence with a filamentous fungus restricted, but also the bacteria able to grow in coexistence with a filamentous fungus and the filamentous fungus having a function proliferate selectively and efficiently. As a result, since the filamentous fungus having a function grows together with the bacteria able to grow in coexistence therewith, thereby cooperatively forming and maintaining an environment in the functional compost, an environment advantageous to the functional filamentous fungus is stably formed in the functional compost.

The filamentous fungus to be inoculated to a compost may be a mycelium, sporophyte or a fruit body of the filamentous fungus or a ground product thereof. Such a material may be ground as is or after being dried, and the material without drying may be preferably ground to an appropriate size by, for example, stirring it with a blade. In cases where mycelia are ground using a homogenizer, the size of the ground mycelia is generally approximately 3 mm in diameter at the largest and many of them have a size of not larger than 3 mm. The ground product has a size of one sporophyte when sporophyte are used, and when fruit bodies are used, the ground product may be made to have a size of, for example, 1 mm×1 mm. Of course, the size of the ground product may be larger or smaller; however, the smaller the size, the more convenient for attaining uniform inoculation.

In cases where such a filamentous fungus or a ground product thereof is inoculated to a compost, although it varies depending on the growth condition of the filamentous fungus, the filamentous fungus or ground product thereof may be inoculated, for example, at an amount of not less than approximately $8 \times 10^{-6}$ g dry fungus/g dry compost, and from the standpoint of the growth stability, preferably at an amount of not less than approximately $8 \times 10^{-4}$ g dry fungus/g dry compost.

In the inoculation step, a functional filamentous fungus is inoculated to a compost in a state in which bacterial activities are restricted. Since the majority of the bacteria and mycobacteria existing in a compost (hereinafter, they may be simply referred to as "bacteria") and a filamentous fungus having a plant disease-controlling function are different in their requirements for the environment for their growth and activities, by making an environment in such a manner that the filamentous fungus can grow and be active, even if the environment is in a state in which bacterial activities are restricted, the filamentous fungus of interest can selectively proliferate.

In this case, it is more preferred that bacteria which can be active and coexist with a filamentous fungus in the same environment (hereinafter, referred to as "bacteria able to grow in coexistence with a filamentous fungus") be present. Since the activities of such bacteria able to grow in coexistence with a filamentous fungus are not restricted even in an environment where the activities of other bacteria that perform composting are restricted, the bacteria can form a stable flora with the filamentous fungus in the compost. Examples of such bacteria able to grow in coexistence with a filamentous fungus include *Virgibacillus halophilus*, and examples thereof include the *Virgibacillus halophilus* I30-1 strain. This fungal strain has been deposited with International Patent Organism Depositary, National Institute of Advanced Industrial Science and Technology, at AIST Tsukuba Central 6, 1-1-1 Higashi, Tsukuba, Ibaraki, Japan, as of May 28, 2008 (Accession No. FERM BP-10975).

The state in which bacterial activities are restricted (the bacterial-activity-restricted state) in the present invention may be any state in which the activities of the bacteria in the compost are restricted, thereby their growth and activities are suppressed. Examples of such state include those selected from the group consisting of a nutrition-restricted state, pH-restricted state and water-restricted state. These restrictive states may be each appropriately selected individually or in combination of two or more thereof in accordance with, for example, the type of the filamentous fungus or bacteria (seed microorganisms) to be used and the environment in which the compost is produced.

The nutrition-restricted state refers to a state in which a slight amount of organic matters remain in the organic waste after the progress in the degree of decomposition and maturation of the compost and, therefore, the compost is so-called "an almost fully-matured state". Such an almost fully-matured state may be determined by, for example, a decrease(s) in the C/N ratio of the compost and/or the $CO_2$ evolution rate therefrom (a high level of the conversion of carbon), and/or transition of the microbial flora. In such almost fully-matured compost, the bacterial activities are restricted since the nutritional condition is extremely poor; however, even in such compost whose nutritional condition restricts the bacterial proliferation, a filamentous fungus may proliferate.

A $CO_2$ evolution rate is defined as a $CO_2$ evolution amount per unit time per unit dry weight of compost, and can be determined easily from measurements of the aeration rate to a compost pile of known weight and the $CO_2$ concentration in the exhaust gas. The $CO_2$ concentration may be measured continuously by a flow cell type infrared absorption $CO_2$ meter. Alternatively, the effluent gas may be once collected in a plastic bag such as a Tedlar bag and measured by gas chromatography or a gas detector tube. There in no particular restriction on the amount of the effluent gas to be collected, and for example the amount which can be collected in a 5 L Tedlar bag may be sufficient.

An example of the usable compost in an almost fully-mature state includes a compost whose $CO_2$ evolution rate after reaching a maximum $CO_2$ evolution rate is $1 \times 10^{-5}$ mol/h/g-dry compost to $3 \times 10^{-5}$ mol/h/g-dry compost. The $CO_2$ evolution rate according to the present invention is based on a measurement by using a Kitagawa gas detector tube 126SA or 126SH (Komyo Rikagaku Kogyo K.K.).

The pH-restricted state refers to a state in which the pH is lower than the optimum pH condition for bacteria. As such a pH-restricted state, the pH may be set, for example, at 4 to 7, preferably 5 to 6.

A water content-restricted state means a state in which the water content is lower than the optimal water content for bacteria. An example of the water content-restricted state includes a state with the water content of 20% to 40% (by mass). The water content may be determined by measuring the compost mass after drying the compost at 105° C. for 48 hours.

These respective activity-restricted states may be appropriately selected individually or in combination in accordance with the growth condition of the filamentous fungus of interest. These activity-restricted states can, by making one of them the rate limiting factor, mitigate other conditions. From the standpoint of more certainly and selectively allowing the filamentous fungus of interest to proliferate, it is more preferred that at least one state be selected from the group consisting the above-described nutrition-restricted state, pH-restricted state and water content-restricted state, and it is more preferred that the condition include at least the nutrition-restricted state. It is still more preferred that all of the above-described nutrition-restricted state, pH-restricted state and water content-restricted state be satisfied. By this, the timing of the inoculation of the filamentous fungus in the composting treatment process can be adjusted, thereby enabling to easily obtain a desired compost.

In the present method of producing a functional compost, a functional compost may also be conducted by acquiring a compost in the state in which the bacterial activities are restricted as described in the above (that is, the later-described compost for proliferating a filamentous fungus), and the method may also further include a step of producing such a compost.

The step of producing compost means a step of allowing degradation of organic matters in an organic waste by inoculating a composting microorganism to the organic waste and culturing it.

As long as a microorganism is inoculated into the organic waste that is to be used as a raw material, the degradation of the organic matter is advanced by culturing for a prescribed time period, resulting in a compost being produced. In order to efficiently carry out composting, it is preferred that the water content, pH and the like be set at the optimum proliferation conditions for the bacteria in the compost. By doing so, rapid composting by bacteria may be attained. In the present invention, composting by setting the water content, pH and the like at the optimum proliferation conditions in order to promptly carry out composting is, as appropriate, referred to as "rapid composting".

As for the conditions of such rapid composting, for example, it is preferred that the temperature, water content, pH and the like inside the compost be adjusted. The optimum conditions for bacterial activities vary depending on the types of the bacteria and the organic waste; however, generally, the conditions may be any condition suitable for the proliferation of ordinary thermophilic bacteria and mycobacteria. The temperature may be set at approximately 60° C. (for example, 50 to 60° C.), the water content may be set at 40% to 60%, and the pH may be set at 8.0 to 8.5. By inoculating seed microorganisms to an organic waste under such optimum conditions and culturing it, a compost to which the above-described filamentous fungus may be inoculated can be promptly obtained in, for example, about 7 days.

For instance, in order to obtain a compost in a nutrition-restricted state, the organic waste may be allowed to decompose and mature until such nutrition-restricted state is attained. Although it varies depending on the type and activity condition of the bacteria, as well as the number of bacteria, in general, the decomposition and maturation of an organic waste may be advanced to almost in maturation by culturing it for 5 to 7 days under the above-described optimum conditions for bacteria, thereby a compost in a nutrition-restricted state (almost fully-matured compost) may be easily obtained. As described in the above, the inoculation of filamentous fungus may be carried out while confirming that the compost is in a nutrition-restricted state using the C/N ratio, $CO_2$ evolution rate or the like as indicator(s).

Further, in order to obtain a compost in a pH-restricted state, the pH of the compost can be adjusted by using an appropriate pH adjusting agent during the decomposition and maturation of organic waste. Examples of the pH adjusting agent which may be used therefor include sulfuric acid, hydrochloric acid, sodium hydroxide, calcium hydroxide and a combination thereof.

A filamentous fungus is inoculated into a compost in a state where bacterial activities are restricted, followed by culturing of the resultant to selectively allow this filamentous fungus to proliferate (proliferation step). In the compost which is in a state where bacterial activities are restricted, because of the selective pressure against bacteria, even if bacteria are present in the compost, the inoculated filamentous fungus proliferates selectively.

Here, in cases where bacteria able to grow in coexistence with the filamentous fungus exist in the compost, such bacteria can also proliferate selectively in the same manner as the filamentous fungus proliferating selectively. These bacteria able to grow in coexistence with the filamentous fungus proliferated together with the filamentous fungus and do not inhibit the filamentous fungus from demonstrating its function. In addition, since the bacteria able to grow in coexistence with the filamentous fungus form a stable flora with the filamentous fungus by proliferating, when the compost is applied to a soil, the bacteria may effectively inhibit those microorganisms originally existing in the soil from infiltrating into the compost. Therefore, even when the functional compost according to the present invention is used in a soil, it is possible to allow the filamentous fungus having a function to stably exist therein.

It is preferred that the culturing temperature be selected in such a manner that the state in which bacterial activities are restricted can be sustained, and the culturing temperature may be set at, for example, 10° C. to 35° C., more preferably 20° C. to 35° C., particularly preferably 27° C. to 30° C. When the culturing temperature is not higher than 35° C., the bacterial proliferation can be effectively suppressed. In contrast, when the culturing temperature is not less than 10° C., an appropriate growth rate of the filamentous fungus can be maintained. In addition, the culturing may be carried out in any aerated condition, and the pH may be also set at 4 to 7, preferably 5 to 6.

The culturing period may be any time period required for the filamentous fungus of interest to sufficiently proliferate within the compost, and it may be, for example, 5 to 7 days. During this period, degradation of the organic matters by the filamentous fungus also progresses; therefore, in cases where a compost in a nutrition-restricted state is used, a fully-matured compost may be obtained at the same time as the completion of the culturing period.

In the compost after the completion of the culturing period, the filamentous fungus sufficiently exists. For example, the filamentous fungus may exist, in terms of the DNA amount in 1 g of dry compost, at an amount of not less than approximately 5 µg/g dry compost, preferably 30 µg/g dry compost.

Since a functional filamentous fungus-containing product obtained in this manner contains *Coprinellus curtus* as the functional filamentous fungus, in cases where the plant pathogenic filamentous fungus belongs to at least one of the genera *Rhizoctonia* and *Fusarium*, the functional filamentous fungus-containing product can exhibit particularly prominent plant disease-controlling effect. Examples of plant disease against which the plant disease control agent according to the present invention can be used include Pak-choi bottom rot, turf ea rot, melon wilt and tomato wilt, and the like.

In cases where this functional filamentous fungus-containing product is used, generally, it may be mixed at an appropriate amount into the subject soil, medium or potting compost. For example, in the case of a plant to which plant disease control is performed, the functional filamentous fungus-containing product is mixed into the soil, medium or potting compost around the plant roots. At this time, the mixing ratio is variable depending on the relative conditions such as the concentration of the pathogenic fungus; however, in general, it is desired that the filamentous fungus having plant disease-controlling function be mixed into the soil at an appropriate fungal amount of 5 µg/g dry compost in terms of the DNA amount, for example, at an amount of about 1 to 20% by mass.

Further, since the compost used in the present invention in a state in which bacterial activities are restricted can be efficiently proliferated a filamentous fungus, the compost is preferable as a material to which the functional filamentous fungus in the present invention is inoculated. As the bacteria able to grow in coexistence with a filamentous fungus that are contained in the present compost for proliferation of the filamentous fungus, *Virgibacillus halophilus* is preferred as described in the above, and for example, it is *Virgibacillus halophilus* I30-1 strain.

The matters described in the above are, as they are, applicable to the bacterial-activities-restricted state of the compost for proliferation of the filamentous fungus, and the state includes at least one state selected from the group consisting of a nutrient-restricted state, pH-restricted state and water content-restricted state. It is also preferred that the bacterial-activities restricted state include a nutrient-restricted state. Further, in such a bacterial-activities-restricted state, not only the bacterial activities can be restricted, but also the filamentous fungus may be selectively grown.

Therefore, by applying the evaluation method according to the present invention to the step of producing a functional filamentous fungus-containing product from such compost for proliferation of filamentous fungus, not only the quality control during the production step and shipment, but also the quality control during the product storage can be simply and accurately carried out. Hence, a functional filamentous fungus-containing product having superior functionality can be stably provided.

EXAMPLES

Examples of the present invention will now be described, provided that the present invention is not limited thereto. Unless otherwise specified, all % used in the examples are by weight (mass).

Example 1

(1) Designing Primers for the GM-21 Strain

Using Clustral X, the nucleotide sequence of 18S (partial), ITS1, 5.8S, ITS2 and 26S (partial) of the GM-21 strain (FIG. 1) and the nucleotide sequences of various filamentous fungi acquired from NCBI (National Center for Biotechnology Information) were aligned, and a region of low conservation was selected from the nucleotide sequence of the GM-21 strain.

Here, the filamentous fungi used in the comparison include *Aspergillus fumigatus* (NBRC No. 5840), *Chaetomium thermophilum* (NBRC No. 30073, No. 30072), *Talaromyces bacillisporus* (NBRC No. 8397), *Mycogone rosea* (NBRC No. 8882), *Humicola grisea* (NBRC No. 9854, No. 4868) and *Penicillium argillaceum* (NBRC No. 31128).

With respect to this region, considering generally employed standards including that the amplification size is 80 to 150 bp; the primer length is 17 to 25 bases; GC content is 40 to 60% (for example, in the vicinity of the 3'-end, it is designed in such a manner that a partially GC- or AT-rich region is not formed); T/C or A/G are not repeated; a complementary sequence of 3 or more bases within or between primers is avoided; and a complementary sequence of 2 or more bases in the primer 3'-end is avoided, or the like, candidate primers were obtained using a known primer design tool such as Primer 3 (Steve Rozen and Helen J. Skaletsky (2000) Primer3 on the WWW for general users and for biologist programmers. In: Krawetz S, Misener S (eds) Bioinformatics Methods and Protocols: Methods in Molecular Biology. Humana Press, Totowa, NJ, pp 365-386 ). From these candidate primers, by modifying as appropriate their annealing position, primer length and the like, the following primer sets A to F including the primer set according to the present invention were obtained (see Table 2).

annealing and elongation at 60° C. for 20 seconds (see Table 4). The composition of the PCR solution and the amplification condition were those recommended by the manufacturer.

TABLE 3

| Reagent | Amount used (μL) |
| --- | --- |
| SYBR Premix EX Taq (2x) | 12.5 |
| PCR Forward Primer (10 μM) | 0.5 |
| PCR Reverse Primer (10 μM) | 0.5 |
| template | 2 |
| dH$_2$O | 9.5 |
| Total | 25 |

(per reaction)

TABLE 2

| Primer | | Name | Annealing Position | Sequence (5'→3') | Number of Bases | Tm (° C.) | GC Content (%) | Note |
| --- | --- | --- | --- | --- | --- | --- | --- | --- |
| Forward | A | GM2125F | 46-68 | gtgttgcatgtagctgcctcctc | 23 | 62.23 | 56.52 | SEQ ID NO: 1 |
| Reverse | | GM2152R | 119-143 | tgacgcgagagttatccagacctac | 25 | 62.12 | 52.00 | SEQ ID NO: 2 |
| Forward | B | GM2127F | 46-68 | gtgttggttgtagctgcctcctc | 23 | 62.12 | 56.52 | SEQ ID NO: 3 |
| Reverse | | GM2172R | 168-188 | tggtaattcgaggagaggcac | 21 | 58.47 | 52.38 | SEQ ID NO: 4 |
| Forward | C | GM2128F | 46-68 | gtgttggatgtagctgcctcctc | 23 | 62.23 | 56.52 | SEQ ID NO: 1 |
| Reverse | | GM2182R | 153-160 | acaggtgccaatcctcg | 17 | 55.51 | 58.82 | SEQ ID NO: 5 |
| Forward | D | GM21715F | 168-189 | gtgcctctcctcgaatttccag | 22 | 60.44 | 54.55 | SEQ ID NO: 6 |
| Reverse | | GM21157R | 234-248 | acgacgcccattgac | 15 | 52.07 | 60.00 | SEQ ID NO: 7 |
| Forward | E | GM21815F | 157-172 | gattgtccactgtgcc | 16 | 52.61 | 56.25 | SEQ ID NO: 8 |
| Reverse | | GM21158R | 234-248 | acgaagcccattgac | 15 | 49.33 | 53.33 | SEQ ID NO: 9 |
| Forward | F | GM2110F | 447-461 | ctgaactgcgtcgag | 15 | 52.07 | 60.00 | SEQ ID NO: 10 |
| Reverse | | GM2111R | 576-592 | gcaagactgaactcgac | 17 | 53.09 | 52.94 | SEQ ID NO: 11 |

(2) Selection of the Optimum Primer I (Comparison Based on the Ct Values)

Used for quantification of the fungal concentration as DNA concentration is a real-time PCR method. The amplified amount of double-stranded DNA synthesized by PCR was monitored in real time using Smart Cycler II (Takara Bio Inc.) as the real-time PCR machine, and the Ct value, which is the number of cycles, was determined by two-step differential analysis of the fluorescence intensity. Since there is a correlation between the Ct value and the initial template DNA amount, the DNA concentration in a sample can be determined by preparing a calibration curve in advance.

The real-time PCR was carried out using Smart Cycler II (Takara Bio Inc.) as the real-time PCR machine, SYBR Premix Ex Taq (Takara Bio Inc.) as the Taq, and SYBR Green I as the intercalator. The composition of the solution used in the PCR is shown in Table 3. Six types of primers, the primers A to F, were used, and as for the amplification condition, initial denaturation was carried out at 95° C. for 10 seconds, followed by 40 cycles of denaturation at 95° C. for 5 seconds and

TABLE 4

| | Number of Cycles | Temperature (° C.) | Time (s) | Fluorescence measurement |
| --- | --- | --- | --- | --- |
| Initial Denaturation | — | 95 | 10 | off |
| Denaturation | 40 | 95 | 5 | off |
| Annealing and Elongation | | 60 | 20 | on |
| Melting Curve Analysis | — | 60→95 | 0.2° C./s | off |

First, in order to verify whether or not the primers efficiently anneal to the GM-21 strain, real-time PCR was carried out with the concentration of the GM-21 strain DNA at 67.9 ng/mL.

The GM-21 strain was cultured at 25° C. for 3 days using Potato-dextrose medium (PD medium). ISOIL for Beads Beating kit (Nippon Gene Co.) was used for extraction and recovery of the GM-21 strain DNA, and Microspin S-300 HR Columns (GE Healthcare UK Ltd., Buckinghamshir, England) was used for DNA purification. The DNA concentration was measured using Quant-ti™ PicoGreen dsDNA Assay Kit (Invitrogen Corporation). All of these equipments were operated in accordance with the manual provided by the respective manufacturers. The results are shown in FIG. 2.

As shown in FIG. 2, since the Ct values obtained by using the primer sets A, B and F were all approximately 19 cycles, it was confirmed that their amplification efficiencies are appropriate.

In contrast, since the Ct values obtained by using the primer sets C, D and E were large, it was found that their amplification efficiencies are poor.

(3) Selection of the Optimum Primer II (Comparison Based on the Ct Values Obtained Using Ultrapure Water)

Next, in order to verify whether or not the primer structures are likely to cause false detection, real-time PCR was carried out in the same manner as in the above (2) using, as the sample, ultrapure water (Milli-Q) not containing DNA. In an evaluation by this method, it may generally be evaluated that the amplification is not considered to be effective due to being non-specific amplification when the Ct value is approximately 30 cycles or more. On the other hand, in the absence of amplification with respect to ultrapure water, it can be evaluated that the primer structures do not cause false detection. The results are shown in FIG. 3.

As shown in FIG. 3, the use of the primer sets B to E resulted in the Ct values of 30 cycles or more; therefore, it can be said that amplification does not occur with respect to the pure water. Further, it can be said that the primer set A, which did not exhibit amplification at all, is highly accurate without false detection.

Therefore, in combination with the above (2), it can be determined that the primer sets A and B are excellent primer sets, and it was demonstrated that the primer set A in particular is a superior primer set.

(4) Quantitative Detection Using the Primer Set A

The quantitative accuracy of the GM-21 strain DNA was verified by real-time PCR using the primer set A.

DNA extracted from the GM-21 strain at a concentration of 1,583 ng/mL was diluted by $10^{-8}$ in eight stages, and using the thus diluted DNA, real-time PCR was carried out in the same manner as in the above (2). The results are shown in FIG. 4.

Figure 4:
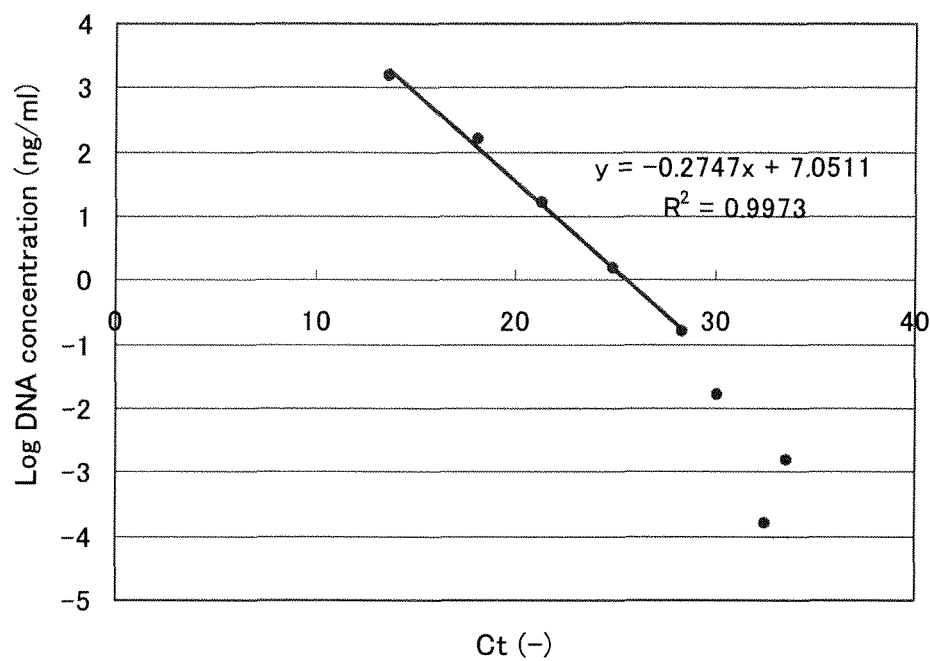
FIG. 4 is a graph showing the relationship between the concentration of the GM-21 strain and the Ct value of the real-time PCR using the primer set A according to Example 1.

As shown in FIG. 4, it was found that detection by the primer set A is possible as long as the amount of the GM-21 strain DNA is appropriate.

In addition, it was demonstrated that, when the DNA concentration was not less than 15.83 μg/mL (Ct value is not greater than 28 cycles), the results showed a linear relationship, which indicates that accurate quantification can be attained. The $R^2$ value of the straight line which represents the correlation coefficient in this case was 0.9973; therefore, it was found that the primer set A is sufficiently quantitative. Here, since the PCR amplification efficiency was about 88.2%, it was found that the amplification efficiency of the DNA was sufficiently high.

Example 2

Quantification in an Environment where Plural Filamentous Fungi Exist

Equivolumes of a solution of DNA of the GM-21 strain (1.58 ng/mL) and a solution of DNA of a filamentous fungus belonging to the genus *Rhizoctonia*, *Rhizoctonia solani* Pak-choi 2, (129.6 ng/mL) were mixed, and real-time PCR was carried out using the primer set A in the same manner as in the above (2).

As a result, the Ct value obtained by the use of the primer set A was 26.16, and the concentration of the GM-21 strain DNA was calculated to be 0.732 ng/mL from the calibration curve of FIG. 4. The concentration of the GM-21 strain DNA in the DNA mixed solution shown in the above (4) is 0.79 ng/mL.

Therefore, it was found that even in cases where DNA that has originated from a filamentous fungus other than the GM-21 strain coexist in a sample, the GM-21 strain DNA can be accurately quantified independently.

Example 3

(1) Specificity to Closely-Related Species

It was examined whether or not the primer set A is effective in distinguishing the GM-21 strain from filamentous fungi belonging to the closely-related genera *Coprinellus* and *Psathyrella*.

In the specificity test, strains of *Coprinus disseminatus*, *Coprinus cinereus*, *Psathyrella candolliana* and *Psathyrella velutina* were used (see Table 5). All of these strains were cultured using a Potato-dextrose medium (PD medium) at 25° C. for 3 days. Alter culturing, their DNA were extracted, recovered and purified and real-time PCR using the prime set A was carried out, in the same manner as in Example 1(2).

Figure 5:
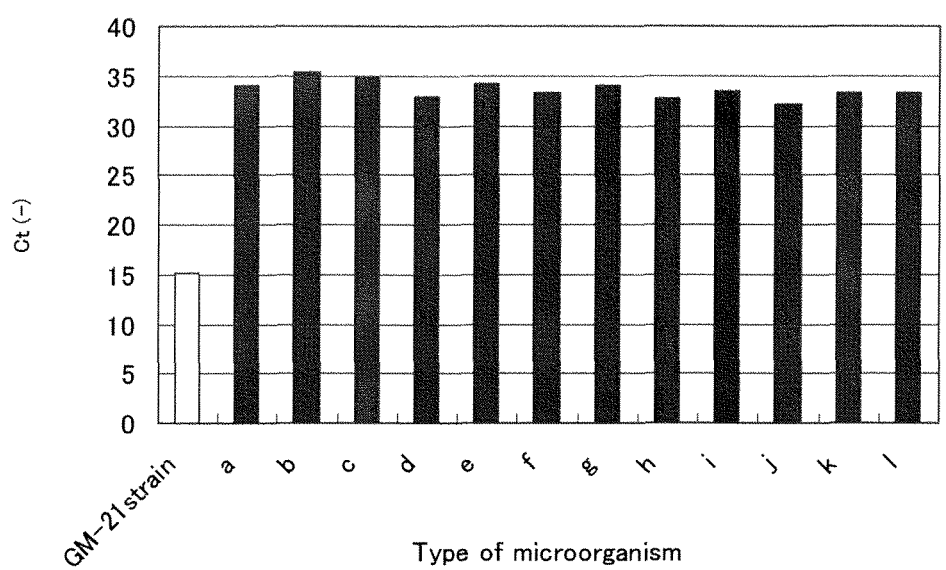
FIG. 5 is a graph showing the Ct values of the real-time PCR using the different types of microorganism and the primer set A according to Example 3.

The results are shown in FIG. 5. It was found that the primer set A can distinguish the GM-21 strain from filamentous fungi belonging to the closely-related genera *Coprinellus* and *Psathyrella*.

(2) Specificity to Filamentous Fungi Normally Existing in Compost

It was examined whether or not the primer set A is effective in distinguishing the GM-21 strain from filamentous fungi normally existing in compost.

In the specificity test, as the filamentous fungi normally existing in compost, strains of *Aspergillus fumigatus*, *Penicillium argillaceum*, *Mycobone rosea*, *Talaromyces bacillisporus*, *Humicola grisea*, *Chaetomium thermophilum* var. *coprophilum* were used (see Table 5). All of these strains were cultured for 3 days under the respective conditions shown in Table 5. After culturing, their DNA were extracted, recovered and purified and real-time PCR was carried out, in the same manner as in Example 1(2).

The results are shown in FIG. 5. It was found that the primer set A can distinguish the GM-21 strain from those filamentous fungi normally existing in compost.

(3) Specificity to Pathogenic Fungi in Soil

It was examined whether or not the primer set A is effective in distinguishing the GM-21 strain from pathogenic filamentous fungi in soil.

Used as the pathogenic filamentous fungus were pathogenic fungus (*Rhizoctonia solani* Pak-choi 2) of pak choi bottom rot disease, pathogenic fungus (*Fusarium oxysporum* f. sp. radicis-lycopersici FO-To-3) of tomato wilt disease, pathogenic fungus (*Fusarium oxysporum* f. sp. melonis FO-Me-2) of melon wilt disease, pathogenic fungus (*Rhizoctonia solani* Kuhn AG2-2 K1) of turf leaf rot disease and pathogenic fungus (*Rhizoctonia solani* lettuce 2) of lettuces bottom rot disease (see Table 5). All of these pathogenic fungi were cultured using Potato-dextrose medium (PD medium) at 25° C. for 3 days. After culturing, their DNA were extracted, recovered and purified and real-time PCR using the prime set A was carried out, in the same manner as in Example 1(2).

Since the Ct values were not less than 30 cycles by which the amplification is not considered to be effective, it can be said that the primer set A does not react to those pathogenic filamentous fungi in soil and, therefore, it was found that the primer set A can distinguish the GM-21 strain from those pathogenic filamentous fungi in soil.

(4) Specificity Filamentous Fungi Normally Existing in Soil

It was examined whether or not the primer set A is effective in distinguishing the GM-21 strain from filamentous fungi normally existing in soil.

In the specificity test, *Penicillium* sp. MY1, *Aspergillus niger* MTP-1, *Mucor* sp. MY 2 and *Rhizopus oryzae* YAN1, which were isolated in laboratory, were used as the filamentous fungi normally existing in soil (see Table 5). All of these filamentous fungi were cultured using Potato-dextrose medium (PD medium) at 25° C. for 3 days. After culturing, their DNA were extracted, recovered and purified and real-time PCR using the prime set A was carried out, in the same manner as in Example 1(2).

Since the Ct values were not less than 30 cycles by which the amplification is not considered to be effective, it can be said that the primer set A does not react to those filamentous fungi normally existing in soil and, therefore, it was found that the primer set A can distinguish the GM-21 strain from those filamentous fungi normally existing in soil.

obtained raw compost mixture was loaded to each mini-reactor at an amount of 15 g to carry out composting.

With regard to the composting conditions, the thus loaded materials were allowed to warm from 30° C. to 60° C. for 0 to 12 hours and then rapidly composted for 192 hours at 60° C. The thus rapidly composted oil cake compost sample was used in the following detection test of the GM-21 strain.

(2) Detection of GM-21 Strain Inoculated to Compost and Soil

Pure-cultured GM-21 strain was inoculated to compost or soil (soil of a flower bed at Shizuoka University, Faculty of Engineering; Hamamatsu-shi, Shizuoka, Japan) at a certain concentration, and it was determined whether or not the GM-21 strain could be recovered. In 200 mL of PD liquid medium, the GM-21 strain was cultured under shaking at 35° C. for 3 days. A suspension of the GM-21 strain (1 mL) homogenized after the culturing was inoculated to the oil cake compost sample prepared in the above (1) after the rapid composting and a soil sample (9 g) in such a manner that the

TABLE 5

| Classification | Filamentous Fungus | Symbol in FIGS. | Medium | Temperature (° C.) |
|---|---|---|---|---|
| A | *Coprinus disseminatus* NBRC 30972 | a | PD | 25 |
|  | *Coprinus cinereus* NBRC 30627 | b | PD | 25 |
|  | *Psathyrella candolleana* NBRC 30365 | c | PD | 25 |
|  | *Psathyrella velutina* NBRC 30529 | d | PD | 25 |
| B | *Aspergillus fumigatus* NBRC 5840 | e | PD | 25 |
|  | *Penicillium argillaceum* NBRC 31128 | f | PD | 25 |
|  | *Mycogone rosea* NBRC 8882 | g | PD | 25 |
|  | *Talaromyces bacillisporus* NBRC 8397 | h | PD | 25 |
|  | *Humicola grisea* var. *thermoidea* NBRC 9854 | i | PD | 35 |
|  | *Humicola grisea* NBRC 4868 | j | PC | 35 |
|  | *Chaetomium thermophilum* var. *coprophilum* NBRC 30073 | k | PC | 35 |
|  | *Chaetomium thermophilum* var. *coprophilum* NBRC 30072 | l | ME | 35 |
| C | *Rhizoctonia solani* Pak-choi 2 |  | PD | 25 |
|  | *Fusarium oxysporum* f. sp. *radieis-lycopersici* FO-To-3 |  | PD | 25 |
|  | *Fusarium oxysporum* f. sp. *melenis* FO-Me-2. |  | PD | 25 |
|  | *Rhizoctonia solani* Kaha AG2-2 K1 |  | PD | 25 |
|  | *Rhizoctonia solani* lettuce 2 |  | PD | 25 |
| D | *Penicillium* sp. MY1 |  | PD | 25 |
|  | *Aspergillus niger* MTP-1 |  | PD | 25 |
|  | *Mucor* sp. MY2 |  | PD | 25 |
|  | *Rhizopus oryzae* YAN1 |  | PD | 25 |

Classification;
A: closely-related fungus,
B: composting fungus,
C: pathogenic fungus,
D: soil fungus Medium;
PD: Potato-dextrose,
PC: Potato carrot,
ME: Malt extract Example 4

(1) Production of Compost

As the raw material, a commercially available oil cake compost (oil cake: manufactured by Fujimi Engei K.K.) was used. An inoculum (Aurace G: manufactured by Matsumoto Institute of Microorganism Co., Ltd.) were adjusted to the initial pH of 7.86 and the water content of 60% and inoculated to the oil cake compost at a dry weight ratio of 19:1. The thus amount is 1/10 in terms of the DNA amount, and the resultants were sufficiently mixed. Thereafter, from the suspension of the GM-21 strain, as well as from the oil cake compost sample after the rapid composting and the soil to which the GM-21 strain was inoculated, in the same manner as in Example 1(2), DNA was extracted and recovered using ISOIL for Beads Beating kit (Nippon Gene Co., Ltd., Toyama) and purified using Microspin S-300 HR Columns (GE Healthcare UK Ltd., Buckinghamshir, England). Real-time PCR using the primer set A was then carried out.

Figure 6:
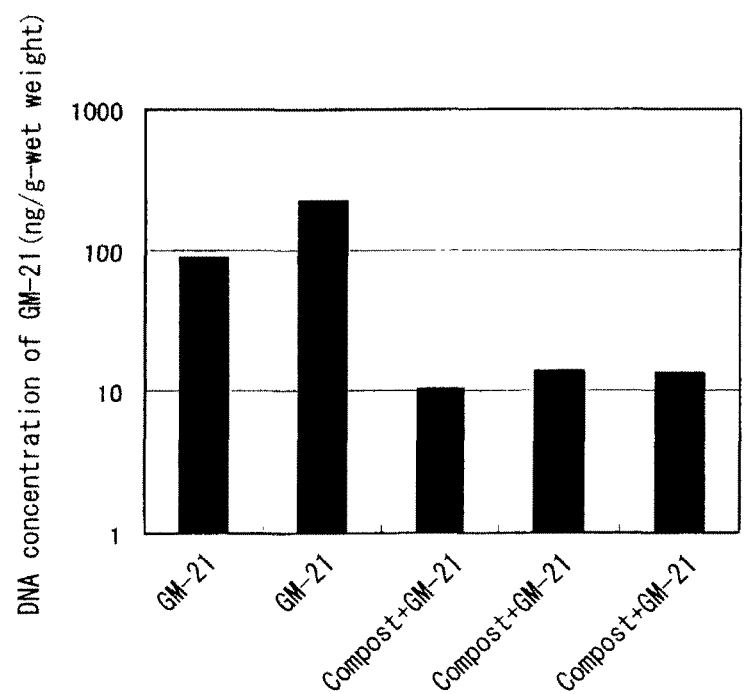
FIG. 6 is a graph showing the concentrations of the GM-21 strain measured by real-time PCR in the GM-21-inoculated suspension and the compost according to Example 4.

The average DNA amount after the rapid composting in the oil cake compost into which the GM-21 strain inoculation suspension (average DNA amount: 189 ng/mL) was inoculated at an amount of 1/10 in terms of the DNA amount, was 12.7 ng/g wet compost, which was an amount of approximately 1/10 (see FIG. 6).

Also for the soil sample into which the GM-21 strain inoculation suspension was inoculated at a concentration of 1/10, the DNA concentration was approximately 1/10, which is similar to that of the oil cake compost after the rapid composting.

From these results, it was confirmed that the primer set A can quantify the GM-21 strain inoculated into compost or soil at a certain concentration.

Example 5

(1) Production of Functional Composts

Using a commercially available oil cake compost rapid composting was carried out at 60° C. for 192 hours, in the same manner as in Example 4. After 8 days (192 hours), a portion of the compost was sterilized using an autoclave at 121° C. for 90 minutes.

The non-sterilized compost and the sterilized compost were mixed as appropriate, and the samples were adjusted to have a bacterial concentration of $10^6$ CFU/g dry compost and $10^3$ CFU/g dry compost, respectively. The pH of the samples was artificially adjusted to approximately pH 6 using 10% by volume of sulfuric acid. Thereafter, the GM-21 strain (0.0068 g dry fungus/mL), which had been cultured in advance under shaking at 35° C. and 100 rpm for 3 days using PD liquid medium, was inoculated to each sample at an amount of 1 mL to a final concentration of 0.00113 g dry fungus/g dry compost.

The samples of which, in this manner, the bacterial concentration was adjusted to $10^6$ CFU/g dry compost and $10^3$ CFU/g dry compost, respectively, and the GM-21 strain was inoculated were cultured at 30° C. for 5 days and composted to obtain functional composts 1 and 2. It is noted here that, since the time of the composting prior to the inoculation of the GM-21 strain, these functional compost samples contain bacteria able to grow in coexistence with the GM-21 strain. These functional compost samples were used in the following detection test of the GM-21 strain.

Figure 7:
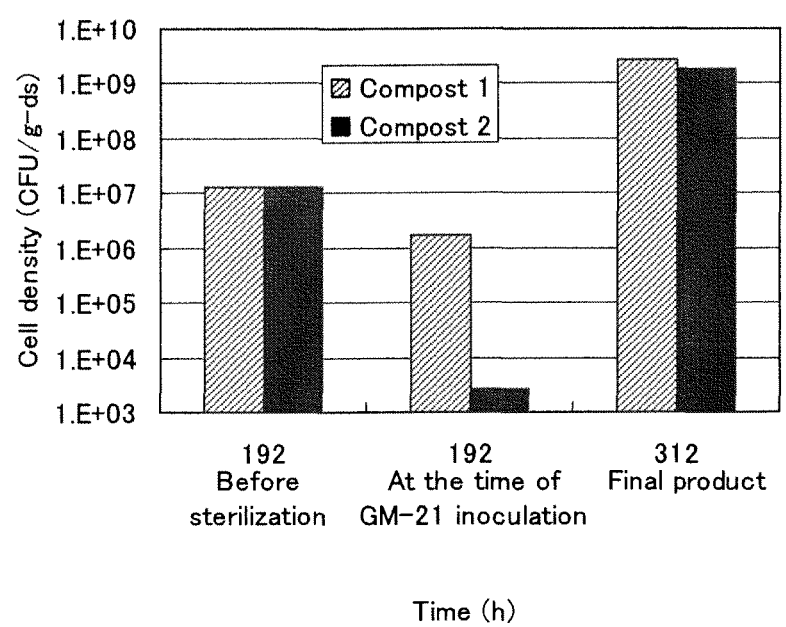
FIG. 7 is a graph showing the change over time in the bacterial concentration in the composts in the step of producing the functional composts according to Example 5.

After completion of the composting, the bacterial concentration of each of the functional compost samples 1 and 2 was measured by dilution plate technique (TS medium, 30° C.). In addition, the concentration of the GM-21 strain in the composts where bacteria exist at a high concentration was measured by real-time PCR method using the primer set A in the same manner as in Example 1(2). FIG. 7 shows the change over time in the bacterial concentration during the composting.

As shown in FIG. 7, the bacterial concentration at the time of inoculation of the GM-21 strain was $10^6$ CFU/g dry compost and $10^3$ CFU/g dry compost for the functional compost samples 1 and 2, respectively; however, at the end of the composting, both samples had a high bacterial concentration of not less than $10^9$ CFU/g dry compost.

<Confirmation of the GM-21 Strain Concentration in the Composts>

The concentration of the GM-21 strain in the production step of the above-described functional compost samples 1 and 2 was measured using real-time PCR method. The measurement was carried out in the same manner as in Example 1(2) by using ISOIL for Beads Beating kit (Nippon Gene Co., Ltd., Toyama) to extract and recover DNA and Microspin S-300 HR Columns (GE Healthcare UK Ltd., Buckinghamshir, England) to purify the DNA, followed by real-time PCR using the primer set A. The results are shown in FIG. 8.

Figure 8:
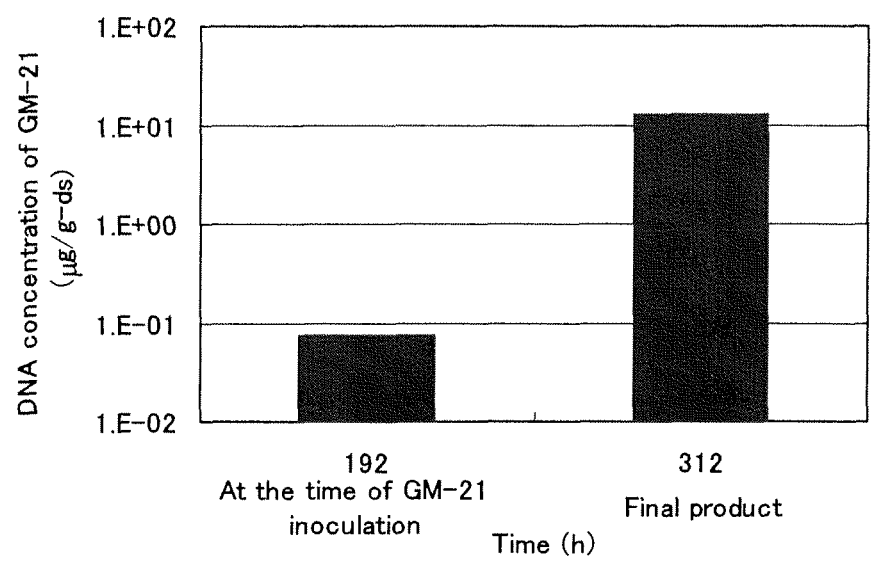
FIG. 8 is a graph showing the change over time in the concentration of the GM-21 strain in the compost in the step of producing functional composts according to Example 5.

FIG. 8 shows the change over time in the concentration of the GM-21 strain during the composting.

As shown in FIG. 8, in the case of the functional compost sample 2, the GM-21 strain proliferated 100-fold or more at the end of the culturing compared to the time of the inoculation of GM-21 strain. In this manner, in the case of the functional compost samples according to the present Example, it was clear that the GM-21 strain can proliferate even if it was inoculated to the samples where bacteria exist. Further, it was also apparent that the GM-21 strain can proliferate regardless of the bacterial amount at the time of the inoculation of the GM-21 strain.

In addition, although, in the present Example, the samples were partially sterilized for use when the GM-21 strain was inoculated, even when the GM-21 strain was inoculated into samples which were rapidly composted without sterilization, the same observations were made regarding the proliferation of the GM-21 strain.

Consequently, it was found that, even if bacteria existed at the time of the inoculation of the GM-21 strain, as long as the composting conditions were controlled, the GM-21 strain proliferates together with the bacteria. It is demonstrated that the primer set A can be used to quantify the change over time of the GM-21 strain inoculated in the process of producing the functional compost.

Thus, it was found that by using the primer set consisting of SEQ ID NO: 1 and SEQ ID NO: 2 according to the present invention, a functional filamentous fungus can be accurately detected. Further, it was found that a sample containing a functional filamentous fungus can be accurately evaluated as well.

The disclosure of Japanese Patent Application No. 2008-214394, which was filed on Aug. 22, 2008, is hereby incorporated by reference in its entirety.

All the literatures, patent applications and technical standards described herein are hereby incorporated by reference to the same extent as in cases where each literature, patent application or technical standard is concretely and individually described to be incorporated by reference.

The invention claimed is:

1. A method of detecting a functional filamentous fungus, the method comprising:
   (a) hybridizing a sample comprising a filamentous fungus, *Coprinellus curtus* with detecting at least one polynucleotide selected from the group consisting of:
      (1) a polynucleotide having a nucleotide sequence shown in SEQ ID NO: 1 and polynucleotide having a nucleotide sequence fully complementary thereto;
      (2) a polynucleotide having a nucleotide sequence shown in SEQ ID NO: 2 and polynucleotide having a nucleotide sequence fully complementary thereto;
      (3) a polynucleotide having a nucleotide sequence shown in SEQ ID NO: 3 and polynucleotide having a nucleotide sequence fully complementary thereto; and
      (4) a polynucleotide having a nucleotide sequence shown in SEQ ID NO: 4 and polynucleotide having a nucleotide sequence fully complementary thereto; and
   (b) detecting hybridization of said polynucleotide with said functional filamentous fungus.

2. The method of detecting a functional filamentous fungus according to claim 1, wherein the detecting of the functional filamentous fungus comprises carrying out PCR using a primer pair including a polynucleotide having the nucleotide sequence shown in SEQ ID NO: 1 or SEQ ID NO: 3 and a polynucleotide having the nucleotide sequence shown in SEQ ID NO: 2 or SEQ ID NO: 4.

3. The method of detecting a functional filamentous fungus according to claim 1, wherein the detecting of the functional filamentous fungus comprises carrying out PCR using a primer pair including a polynucleotide having the nucleotide sequence shown in SEQ ID NO: 1 and a polynucleotide having the nucleotide sequence shown in SEQ ID NO: 2.

4. The method of detecting a functional filamentous fungus according to claim 1, wherein the functional filamentous fungus, *Coprinellus curtus*, is *Coprinellus curtus* GM-21 (NITE BP-37).

5. The method of detecting a functional filamentous fungus according to claim 1, wherein the sample is at least one selected from the group consisting of a soil sample, a compost sample, a cultured sample and an immobilized sample.

6. A method of evaluating a product containing a functional filamentous fungus, *Coprinellus curtus*, the method comprising:
   carrying out quantitative PCR on a sample from the product containing the functional filamentous fungus using a primer pair including a polynucleotide having a nucleotide sequence shown in SEQ ID NO: 1 or SEQ ID NO: 3 and a polynucleotide having a nucleotide sequence shown in SEQ ID NO: 2 or SEQ ID NO: 4; and
   evaluating, based on the results of the quantitative PCR, a presence or a concentration of the functional filamentous fungus, *Coprinellus curtus*, in the product containing the functional filamentous fungus.

7. The method of evaluating a product containing a functional filamentous fungus according to claim 6, wherein the primer pair includes a polynucleotide having the nucleotide sequence shown in SEQ ID NO: 1 and a polynucleotide having the nucleotide sequence shown in SEQ ID NO: 2.

8. The method of evaluating a product containing a functional filamentous fungus according to claim 6, wherein the product containing a functional filamentous fungus is a compost obtained by a method which comprises inoculating the functional filamentous fungus, *Coprinellus curtus*, into a compost in a bacterial-activity-restricted state; and culturing so as to proliferate the filamentous fungus selectively.

9. The method of evaluating a product containing a functional filamentous fungus according to claim 8, wherein the functional compost further contains bacteria able to grow in coexistence with a filamentous fungus, the bacteria being active under the growth conditions of the filamentous fungus.

10. The method of evaluating a product containing a functional filamentous fungus according to claim 8, wherein the functional compost further contains bacteria able to grow in coexistence with a filamentous fungus, *Virgibacillus halophilus* I30-1 (FERM BP-10975), which is active under the growth conditions of the filamentous fungus.

11. A primer pair comprising the following polynucleotides:
   (1) a polynucleotide having a nucleotide sequence shown in SEQ ID NO: 1 or SEQ ID NO: 3; and
   (2) a polynucleotide having a nucleotide sequence shown in SEQ ID NO: 2.

12. A polynucleotide, the set comprising at least two polynucleotides selected from:
   (a) at least one polynucleotide selected from the group consisting of:
      (1) a polynucleotide having a nucleotide sequence shown in SEQ ID NO: 1 or a nucleotide sequence fully complementary thereto;
      (2) a polynucleotide having a nucleotide sequence shown in SEQ ID NO: 2 or a nucleotide sequence fully complementary thereto;
      (3) a polynucleotide having a nucleotide sequence shown in SEQ ID NO: 3 or a nucleotide sequence fully complementary thereto; and
      (4) a polynucleotide having a nucleotide sequence shown in SEQ ID NO: 4 or a nucleotide sequence fully complementary thereto, and
   (b) at least one polynucleotide selected from the group consisting of:
      (1) a polynucleotide having a nucleotide sequence shown in SEQ ID NO: 1 or a nucleotide sequence fully complementary thereto;
      (2) a polynucleotide having a nucleotide sequence shown in SEQ ID NO: 2 or a nucleotide sequence fully complementary thereto; and
      (3) a polynucleotide having a nucleotide sequence shown in SEQ ID NO: 4 or a nucleotide sequence fully complementary thereto.

13. The polynucleotide set according to claim 12, wherein the polynucleotide set consists of the following:
   a polynucleotide having a nucleotide sequence shown in SEQ ID NO: 1 or a nucleotide sequence fully complementary thereto; and
   a polynucleotide having a nucleotide sequence shown in SEQ ID NO: 2 or a nucleotide sequence fully complementary thereto.

14. A polynucleotide, consisting of one of the following:
   (1) a polynucleotide having a nucleotide sequence shown in SEQ ID NO: 1 or a nucleotide sequence fully complementary thereto; or
   (2) a polynucleotide having a nucleotide sequence shown in SEQ ID NO: 2 or a nucleotide sequence fully complementary thereto; or
   (3) a polynucleotide having a nucleotide sequence shown in SEQ ID NO: 4 or a nucleotide sequence fully complementary thereto.

* * * * *